United States Patent
Narayanan et al.

(10) Patent No.: US 7,019,046 B2
(45) Date of Patent: Mar. 28, 2006

(54) AQUEOUS SUSPENSION AGENT FOR WATER INSOLUBLE COMPOUNDS

(75) Inventors: Kolazi S. Narayanan, Wayne, NJ (US); Domingo I. Jon, New York, NY (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 10/209,122

(22) Filed: Jul. 31, 2002

(65) Prior Publication Data

US 2004/0024099 A1 Feb. 5, 2004

Related U.S. Application Data

(63) Continuation-in-part of application No. 09/924,191, filed on Aug. 8, 2001, now Pat. No. 6,624,242.

(51) Int. Cl.
*C08K 11/00* (2006.01)

(52) U.S. Cl. .................. 523/122; 504/101; 504/116.1; 504/360; 504/361; 524/9; 524/10; 524/73; 524/516; 524/612; 527/400

(58) Field of Classification Search .................. 524/9, 524/10, 73, 612, 516; 527/400; 504/101, 504/116.1, 360, 361; 523/122
See application file for complete search history.

(56) References Cited

U.S. PATENT DOCUMENTS

| | | | | |
|---|---|---|---|---|
| 2,778,768 A | * | 1/1957 | Brown et al. | 514/483 |
| 3,116,326 A | * | 12/1963 | Lamb | 564/8 |
| 3,359,225 A | * | 12/1967 | Weisend | 524/2 |
| 3,393,990 A | * | 7/1968 | Geary | 504/361 |
| 3,891,454 A | * | 6/1975 | Cunningham et al. | 106/719 |
| 5,228,915 A | * | 7/1993 | Crema et al. | 106/724 |
| 5,231,070 A | * | 7/1993 | Narayanan et al. | 504/113 |
| 5,597,574 A | * | 1/1997 | Narayanan et al. | 424/401 |
| 5,629,261 A | * | 5/1997 | Narayanan et al. | 504/361 |
| 5,698,211 A | * | 12/1997 | Narayanan | 424/409 |
| 5,776,856 A | * | 7/1998 | Narayanan | 504/361 |
| 6,156,803 A | * | 12/2000 | Curry et al. | 514/772.2 |
| 6,492,322 B1 | * | 12/2002 | Cooper et al. | 510/516 |
| 6,624,242 B1 | * | 9/2003 | Curry et al. | 524/808 |

* cited by examiner

*Primary Examiner*—Bernard Lipman
(74) *Attorney, Agent, or Firm*—William J. Davis; Walter Katz

(57) ABSTRACT

This invention relates to an improved aqueous suspension concentrate for water insoluble chemicals comprising a mixture of an anionic suspension agent and a homo- and/or a co-polymer of a heterocyclic vinyl lactam combined in a mole ratio of between about 0.1:1 and about 10:1.

13 Claims, No Drawings

AQUEOUS SUSPENSION AGENT FOR WATER INSOLUBLE COMPOUNDS

This application is a continuation-in-part of U.S. patent application Ser. No. 09/924,191, filed on Aug. 8, 2001 by James F. Curry et al and issued as U.S. Pat. No. 6,624,242 B2.

CROSS-REFERENCE TO RELATED PATENT

This application is related to U.S. Pat. No. 6,156,803 which discloses a partially neutralized alkyl vinyl ether-maleic acid half ester copolymer as a dispersing agent for insoluble agriculturally active chemicals.

FIELD OF THE INVENTION

The present invention concerns an aqueous flowable suspension concentrate for insoluble active chemicals, particularly agriculturally active compounds, although the present mixture can also be employed to form stable high load suspensions of water insoluble pharmaceuticals, hydrophobic metal oxides, e.g. oxides of titanium and iron, activated carbon and pigments including organic dyes.

DESCRIPTION OF THE PRIOR ART

Numerous delivery systems and formulations have been proposed to provide aqueous solutions of substantially water insoluble agriculturally active chemicals. Such compositions include those disclosed in U.S. Pat. No. 5,300,529 referred to above and in U.S. Pat. Nos. 5,283,229; 5,250,499; 5,176,736; 5,160,528; 5,156,666 and 5,071,463. The later group of patents all involve solubilization of the water insoluble active component with suitable non-polymeric lactams. In the field, however, it is desirable that the active component retains its hydrophobic character both in the concentrate and diluent compositions so as to extend activity on the plant under climatic conditions such as rainfall and provide systemic effects. Additionally, many of the prior formulations limit the load of the active compound to achieve stability or have been found to provide only ephemeral suspensibility. Still further, many of the suspension agents presently in use are specific to a limited group of active compounds.

Accordingly, it is an object of this invention to provide a non-specific suspension delivery system which preserves the insolubility and stability of the active component in an active high load formulation.

Another object is to provide a suspension delivery system having extended storage properties in both the concentrate and diluted solutions thereof.

Another object is to provide a commercially feasible and relatively inexpensive suspension formulation which is easily prepared and which is effective for disparate active chemical species.

Still another object is to provide a suspension concentrate which retains its stability over an extended range of dilution with water to achieve a convenient sprayable composition.

These and other objects of the invention will become apparent from the following description and disclosure.

SUMMARY OF THE INVENTION

In accordance with this invention there is provided an aqueous concentrate containing between about 20 and about 85 wt. % of a water insoluble active component or mixture of active components; between about 0.5 and about 15 wt. % of at least one anionic dispersant as the primary suspension agent and from about 0.1 to about 10% lactam homo- and/or co-polymer as a modifier or secondary suspension agent. In addition, the aqueous concentrate may optionally contain between about 0.1 and about 25 wt. % of a conventional excipient where desired or needed for a particular use. Such inert materials include a thickening agent, a defoaming agent, an organic diluent and/or an anti-freezing agent and the like.

DETAILED DESCRIPTION OF THE INVENTION

The primary dispersant in the present composition is an anionic copolymer such as a lignosulfonate or metal salt thereof, e.g. commercially available as POLYFON or REAX, supplied by Westvaco Inc.; a sulfonated naphthalene/formaldehyde condensate, e.g. MORWET, supplied by Witco; UFOXANE or MARESPERSEs supplied by Lignotech Co.; the sodium salt of alkyl vinyl ether/maleic acid half ester copolymer, a polyacrylate such as methacrylate/ethylacrylate copolymer, an alpha-olefin/maleic acid copolymer and any other polymeric anionic dispersant capable of dispersing hydrophobic compounds in water. Desirably the monomer of the anionic copolymer contains 1–4 anionic sites per mole of repeat units.

The lactam modifier of the composition can be the homopolymer of vinyl caprolactam or vinyl pyrrolidone either optionally substituted on the ring or in the vinyl group with lower alkyl ($C_1$ to $C_4$ alkyl) or a mixture of these homopolymers. Alternatively the modifier can be a copolymer of vinyl caprolactam and/or vinyl pyrrolidone, e.g. vinyl caprolactam/vinyl pyrrolidone copolymer, vinyl pyrrolidone/vinyl acetate, vinyl methylpyrrolidone/vinyl acetate, methylvinyl pyrrolidone/acrylic acid. The lactam modifiers have a weight average molecular weight of between about 5,000 and about 100,000 consistant with a Fikentscher K-value of from about 10 to about 120. In the concentrate mixture, the lactam polymer coils around and coats at least a portion of the active water insoluble moiety thus reducing its surface hydrophobicity while retaining intrinsic hydrophobic character of the insoluble active component. The lactam coating associates with the anions of the primary dispersant to provide a concentrate of improved stability and permits high load active compositions for disparate hydrophobic species which are not otherwise suspendable.

Preferably the concentration of lactam polymer in the concentrate composition is between about 0.3 and about 5 wt. % and the concentration of the primary dispersant in the concentrate is between about 0.1 and about 10, preferably 0.5–5, wt. %. Generally, a mole ratio of anionic dispersant to lactam polymer of between about 0.1:1 and about 3 1 is recommended.

The active component of the present concentrate is a particulate water insoluble compound or a hydrophobic mixture of such compounds and is preferably an active animal fumigant or agricultural chemical including nematocides, fungicides, insecticides, herbicides and mulliscides as well as agricultural fertilizers, nutrients, plant growth accelerants or growth controlling agents or any other hydrophobic chemical having properties which are suitable for agricultural uses in terms of application to plants or domestic houshold or animal uses for controlling insects and pests. Particularly, such chemicals would normally take the form of water-immiscible or oily liquids and/or solids which are substantially insoluble in water. By the term "substantially insoluble", it is meant that for all practical purposes, the solubility of the compound in water is insufficient to make the compound practicably usable in a spray-on or dip end use without some modification either to increase its solubility or dispersability in water, so as to increase the compound's bioavailability or avoid the use of excessively large volumes of solvent.

Suitable agriculturally acive chemicals which can be used with the present inention include insecticides, such as, cyclocompounds, carbamates, animal and plant derivatives, synthetic pyrethroids, diphenyl compounds, non-phosphates, organic phosphates, thiophosphates, and dithiophosphates. (See Agricultural Chemicals, Book I, Insecticides, 1989 Revision by W. T. Thomson, Thomson Publications.) Typical of the insecticides are:

| | |
|---|---|
| Cyclocompounds: | 6,7,8,9,10,10-hexachloro-1,5,5a,6,9,9a-hexahydro-6,9-methano-2,4,3-benzodioxathiepin-3-oxide |
| Carbamates: | 2-isopropyl phenyl-N-methyl carbamate; 2-(1,3-dioxolan-2-yl)phenylmethyl carbamate; 2,3-isopropylidine dioxyphenyl methyl carbamate; |
| Animal and Plant Derivatives | chlorinated hydrocarbons derived from Southern pine naturally occurring lactone glycoside; |
| Synthetic Pyrethroids: | (±) α-cyano-3-phenoxybenzyl (±) cis, trans 3-(2,2-dichlorovinyl)-2,2-dimethyl cyclopropane carboxylate; (±) cyano (3-phenoxyphenyl) methyl (±)-4-(difluoromethoxy) α-(1-methylethyl) benzene acetate; |
| Phenoxy Compounds and Non-Phosphate: | 2,2-bis(p-methoxy phenyl)-1,1,1,trichloroethane; 1,3,5,tri-n-propyl-1,3,5-triazine-2,4,6(1H,3H,5H)trione; ethyl(2E, 4E)-3,7,11-trimethyl-2,4-dodeca dienoate; 1-decycloxy 4-[(7-oxa-oct-4-ynyl)]-oxybenzene; |
| Organic Phosphates: | dimethyl phosphate ester of 3-hydroxy-N,N-dimethyl-cis-crotonamide 2-chloro-1-(2,4-dichloro phenyl)vinyl diethylphosphate; 4-(methyl thio)phenyl dipropyl phosphate; |
| Thiophosphates: | 0,0-diethyl-0-4-nitrophenyl phosphorothioate 0,0-diethyl-0-(2, isopropyl-6-methyl-5-pyrimidinyl) phosphorothioate; 2-diethylamino-6-methyl pyrimidine-4-yl dimethyl phosphorothioate; |
| Dithiophosphates: | 0,0-dimethyl phosphorodithioate ester of diethylmercapto succinate; 0-ethyl-S-phenyl ethyl phosphorodithioate. |

Typical herbicides include phenoxy compounds, benzoic, acetic, and phthalic acids, aniline derivatives, nitriles, amides, acetamides, anilides, carbamates, thiocarbamates, and heterocyclic nitrogen derivatives, e.g., triazines, pyridines, pyridazones, picolinic acid, and urea derivates and phosphates. (See Agricultural Chemicals, Book II, Herbicides, 1986–87 Edition, W. T. Thomson, Thomson Publications, Fresno, Calif. 93791.) Exemplary of the above compounds are:

| | |
|---|---|
| Phenoxy Compounds: | 2,4-dichlorophenoxy acetic acid 2,4,5-trichloro phenoxyacetic acid; 4-(2,4-dichlorophenoxy) butyric acid; S-ethyl 2 methyl-4-chlorophenoxythioacetate; 2-methyl-4-chloro-phenoxy acetic acid; methyl 5-(2,4-dichloro-phenoxy-2-nitrobenzoate; |

-continued

| | |
|---|---|
| Benzoic and Acetic Acids of Phthalic Compounds: | 3,6-dichloro-o-anisic acid 4-chloro-2-oxo benzothiazolin-3-yl acetic acid; N-1-Naphthyl-phthalamic acid; |
| Nitriles and Aniline Derivatives: | 3-5-dibromo-4-hydroxybenzo-nitrile; α,α,α,trifluoro-2,6-dinitro-N,N-dipropyl-p-tolinidine; N-(1-ethylpropyl)-2,6-dinitro-3,4-xylidine; |
| Amides, Acetamides, Anilides: | N,N-diethyl-2-(1-naphthalenyl oxy)-propionamide; 2,6-dimethyl-N-2' methoxyethyl-chloro-acetanilide; 3',4'-dichloro-propionanilide; α-chloracetic-N-(3,5,5-trimethylcyclohexen-1-yl)-N-isopropylamide 4-benzyl-N-isopropyl trimethyl acetamide; |
| Thiocarbamates: | S-ethyl dipropyl thiocarbamate; |
| Urea Derivatives: | 3-(5-tert-butyl-3-isoxazoyl)-1,1-dimethyl urea; N-(2,6-trifluoro-benzoyl)-N'-[2,5-dichloro-4-(1,1,2,3,3,3-hexafluoropropyloxy)phenyl]urea; |
| Pyrrolidone Derivatives: | 1-(m-trifluoro methyl phenyl)-3-chloro-4-chloromethyl-2-pyrrolidone; |
| Amino Acid Derivatives: | methyl N-benzoyl-N-(3-chloro-4-fluorophenyl)-DL alarinate; N-chloroacetyl-N-(2,6-diethylphenyl)-glycine ethyl ester; |
| Carbamates: | Isopropyl-m-chlorocarbanilate; 3-ethoxy (carbonyl aminophenyl)-N-phenyl carbamate; |
| Heterocyclics: | 4-amino-3,5-dichloro-6-fluoro-2-pyridyloxy acetic acid; 4-(1,2-Dimethyl-N-propyl amino)-2-ethyl amino-6-methyl thio-S-triazine; 2-[4,5-dihydro 4-methyl-4-(1-methylethyl)-5-oxo-1 H-imidazoyl-2yl-3-byridinecarboxylic acid; 2-[3,5-dichlorophenyl]-2-(2,2,2-trichloroethyl) oxinane; butyl-9-hydro-fluorene-(9)-carboxylate; 2-[1-(ethoxy imino) butyl]-3-hydroxy-5-(2H-tetra hydro thiopyran-3-yl)-2-cyclohexene-ione; 2-(2 chlorophenyl)methyl-4,4-dimethyl-3-iso oxazolidinone; |
| Phosphates: | 0-ethyl-0-(3-methyl-6-nitro phenyl) N-sec-butyl phosphoro thio amidate. |

Typical fungicides include (See Agricultural Chemicals, Book IV, Fungicides, 1989 Revision, W. T. Thomson, Thomson Publications, Fresno, Calif. 93791):

| | |
|---|---|
| Organic Compounds: | 2,5-dimethyl-N-Cyclohexyl-N-methoxy-3-furan carboxamide; 5-Ethyoxy-3-trichloromethyl-1,2,4-thiadiazole; 3-(2-methyl piperidino) propyl 3,4-dichlorobenzoate; N,N'-(1,4-piperazinediyl bis(2,2,2-trichloro) ethylidene) bis formamide; Tetramethyl thiuram disulfide; 0-Ethyl-S,S,diphenyl-dithiophosphate; 5,10-dihydro-5,10-dioxo naphtho(2,3,9)-p-dithiin-2,3-dicarbonitrile; 2-(Thiocyano methyl thio)benzothiazole; α-2-(4-chlorophenyl)ethyl]-α-(1,1-dimethyl ethyl)-1 H-1,2,4-triazole-1-ethanol; Iodopropargyl butyl carbonate; Tetra chloro iso phthalonitrile |
| Morpholines: | N-tridecyl-2,6-dimethyl morpholine; 4-N-dodecyl-2,6-dimethyl morpholine |

Typical fumigants, growth regulators, repellants, and rodenticides include (See Agricultural Chemicals, Book II, Fumigants, 1988–1989 Revision, W. T. Thomson, Thomson Publications, Fresno, Calif. 93791):

| | |
|---|---|
| Growth Regulants: | 1,2 Dihydro-6-ethyoxy-2,2,4-trimethylquinoline; (2-chloroethyl) phosphoric acid; 4-[acetamino methyl]-2-chloro-N-(2,6-diethyl phenyl acetamide; Benzoic acid, 3,6 dichloro-2-methoxy,2-ethoxy-1-methyl-2-oxo ethyl ester; |
| Repellants: | 0,0-dimethyl-0-[(4-methyl thio)-m-tolyl] phosphorothioate; Tertiary butyl-sulfenyl dimethyl dithio carbamate; |
| Seed Softener: | 2-chloro-6-(trichloromethyl) pyridine; 5-ethoxy-3-trichloromethyl-1,2,4-thiadiazole; N-phenyl-N'-1,2,3-thiadiazol-5-yl urea. |

Pesticides may be characterized by their physical properties, depending on their physical state at normal or ambient conditions, i.e., between 40° F. and 90° F. and their solubility or miscibility with water or other common organic solvents, e.g., aromatics, such as, toluene, xylene, methylated and polyalkylated naphthalenes, and aliphatic solvents.

Based on the physical properties, the pesticides may be classified into two groups. The first group includes those which are oily liquids at ambient temperatures and are immiscible with water. Specific pesticides include:

Common esters of 2,4-dichlorophenoxyacetic acid,
Common esters of 2,4,5-trichlorophenoxyacetic acid,
Common esters of 2-(2,4-dichlorophenoxy) propionic acid,
Common esters of 2-(2,4,5-trichlorophenozy) propionic acid,
Common esters of 2,4-dichlorobutyric acid,
Common esters of 2,methoxy-3,6-dichlorobenzoic acid,
Common esters of 2-methyl-4-chlorophenoxyacetic acid,
Piperonyl butoxide 3,4-methylenedioxy-6-propyl benzyl n-butyl diethylene glycol ether,
Bromophos ethyl: 0,0-diethyl-0-2,5-dichloro-4-bromophenyl thionophosphate,
N-(2-mercaptoethyl) benzene-sulfenamide (BETASAN®),
Isobornyl Thiocyanoacetate (Thanite®),
loxynil ester of octanoic acid,
Molinate S-ethyl hexahydro-1H-azepine-1-carbothioate,
PP 511 O,O-dimethyl-(2-diethylamine 4-methyl-6-pyrimidinyl) carbamate,
PP 211 O,O-diethyl O-(2-diethylamine-4-methyl-6-pyrimidinyl) phosphorocarbamate,
Chlordane,
5-Ethoxy-3-(trichloromethyl)-1,2,4-thiadiazole (TERRAZALE®),
Ethyl-s-s-dipropyl-phosphodithioate (MOCAP®),
S-Ethyl dipropylthiocarbamate (EPTAM®),
S-Ethyl diisobutylthiocarbamate (SUTAN®),
S-n. propyl-di-n-propylthiocarbamate (VERNAM®),
S-propyl butylethylthiocarbamate (TILLAM®),
S-ethyl ethylcyclohexylthiocarbamate (RO-NEET®),
Malathion (S-(1,2-dicarboxyethyl)-O,O-dimethyl phosphorodithioate),
Diazinon (O,O-diethyl,O-(2-isopropyl-4-methyl-6-pyrimidinyl) phosphorothioate,
O-Ethyl-S-phenyl-ethylphosphonodithioate (DYFONATE®),
Toxaphene (Octachlorocamphene),
Bromoxynil (3,5-dibromo-4-hydroxy benzonitrile ester of n.octanoic acid,
2-chloro-N-2,6-diethylphenyl-N-methoxymethylacetamide (LASSO®),
Diallate S-2,3-dichloroallyl N,N-diisopropylthiolcarbamate,
Triallate S-2,33-trichloroallyl N,N-diisopropylthiolcarbamate.

The second group comprises those pesticides which are solids at ambient temperatures and for all practical purposes, insoluble in water.

2,4,5-T (2,4,5-trichlorophenoxy acetic acid)
Monuron (3-(p-chlorophenyl)-1,1-dimethyl urea)
Diuron (3-(3,4-dichlorophenyl)-1,1-dimethyl urea)
Bromacil (5 bromo-3-sec. butyl-6-methyl uracil)
Isocil (5 bromo-3-isopropyl-6-methyl uracil)
Linuron (3-(3,4 dichlorophenyl)-1-methoxy-1 methyl urea
Atrazine (2-chloro-4-ethylamino-6 isopropylamino-s-triazine)
Simazine (2-chloro-4,6,-bis (ethylamino)-s-triazine
Dodine (n-dodecylguanidine acetate)
Thiram (tetramethylthiuram disulfide)
N-(mercaptomethyl)phthalimide s—(o,o dimethylphosphoro-dithioate) (IMIDAN®)
Lindane (gamma 1,2,3,4,5,6 hexachlorocyclohexane)
Folpet (N-trichloromethylphthalimide)
Manazon (s-(4,6-diamino-1,3,5-triazin-2-yl methyl)-dimethylphosphorothiolthionate)
Barban (4-chloro-2 butynyl m-chlorocarbanilate)
Tricumba 2-methoxy-3,5,6-trichlorobenzoic acid
Trifluralin (2,6-dinitro-N,N-dipropyl-4-trifluoro-methylamiline) (2,3 dihydro-5-carboxanilido-6-methyl-1,4-oxathiin) (VITAVAX®)
2,4-dichlorophenoxyacetic acid
4-(4-chloro-2 methylphenoxy) butyric acid
2-(2,4-dichlorophenoxy) propionic acid
loxynil: 3,5 diiodo-4-hydroxybenzonitrile
Bromoxyni 1: 3,5 dibromo-4-hydroxybenzonitrile
Carbaryl: 1-naphthyl-N-methylcarbamate
Methoxychlor: 2,2,-Bis(p-methoxyphenyl)-1,1-trichloroethane
PP 781: 4(2-chloro phenylhydrazono)-3-methyl-5-isoxazolone*
PP 675: 5-butyl-2-dimethylamino-4-hydroxy-6-methyl pyrimidine*
PP 062: 5,6-dimethyl-2-dimethylamino-4 pyrimidinyl dimethylcarbamate*
PP 149: 5-n-butyl-2 ethylamino-4-hydroxy-6 methylpyrimidine*

* Manufactured by Imperial Chemical Industries Limited

C 6313 N'-(4-bromo-3-chlorophenyl)-N-methoxy-N-methylurea
C 6989 2,4'-dinitro-4-trifluoromethyl-diphenylether
Chloroxuron N'-4-(chlorophenoxy) phenyl-NN-dimethylurea
Dichlobenil 2,6-dichlorobenzonitrile
Diphenamid NN-dimethyl-2,2-diphenylacetamide
Fenac 2,3,6-trichlorophenylacetic acid
Fluometuron N'-(3-trifluoromethylphenyl)-N N-dimethylurea
GS 14260 4-ethylamino-2-methylthio-6-t-butyl-amino-1,3,5-triazine
PCP Pentachlorophenol
Lenacil 3-cyclohexyl-6,7-dihydro-1H-cyclo-pentapyrimidine-2,4-(3H ,5H)-dione
Pyrazon 5-amino-4-chloro-2-phenyl-3-pyridazone
Metrobromuron N'-(4-bromophenyl)-N-methoxy-N-methylurea
Metoxymarc N-(4-methoxybenzoyl)-N-(3,4-dichlorophenyl)-N',N'-dimethylurea
Neburon N-butyl-N'-(3,4-dichlorophenyl-N-methylurea
NIA 11092 1,1-dimethyl-3-[3-(n-t-butyl carbamyloxy) phenyl] urea
Mecoprop 2-(4-chloro-2 methylphenoxy)propionic acid
Monolinuron N'-(4-chlorophenyl)-N-methoxy-N-methylurea
Nitrofen 2,4-dichlorphenyl 4-nitrophenylether
Propanil N-(3,4-dichlorophenyl)propionamide Pyriclor 2,3,5-trichloro-4-pyridinol
Solan 3'-chloro-2-methyl-p-volerotoluidide
Terbacil 5-chloro-3-t-butyl-6-methyluracil
UC 22463 (SIRMATE)-3,4-dlchlorobenzyl N-methylcarbamate
WL 9385 2-Azido-4-ethylamino-6-t-butylamino-s-triazine
Propachlor 2-chloro-N-isopropylacetanilide
CP 50144 2-chloro-N-2,6-diethylphenyl-N-methoxymethyl acetamide
CP 31675 2-chloro-N-(2 methyl-6-t-butylphenyl) acetamide
Cypromid 3',4'-dichlorocyclopropane carboxanilide
Fenuron NN-dimethyl-N'phenylurea
Chlorbromuron N'-(4-bromo-3-chlorophenyl)-N-methoxy-N-methyl urea
Ametryne 2-methylmercapto-4-ethylamino-6-isopropyl-amino-s-triazine
Prometryne 2-methylmercapto-4,6-bisisopropyl amino-s-triazine
DCPA dimethyl 2,3,5,6, tetrachloroterephthalate
Benefin N-butyl-N-ethyl-2,2,2-trifluoro-2,6-dinitro-p-toluidine
Nitralin 2,6-dinitro-4-methylsulfonyl-NN-dipropyl-aniline
PP 493 2,6-difluoro-3,5-dichloro-4-hydroxy pyridine
CNP 2,4,6-trichlorophenyl-4'-nitrophenyl ether
Pentachloro nitrobenzene
1-(butile carbamoyl)-2-benzimidazol carbamic acid, methyl ester (BENLATE®)

The concentration of the active component in the concentrate and in the diluted product can vary widely depending on the ultimate use, severity of the infection or infestation or other considerations including the degree of dilution desired to produce a viable spray or animal dip, color intensity, etc. For the purposes of agricultural uses, a concentration of between about 0.1 and about 5 wt. % concentrate in the diluted product is usually preferred.

The concentrate can optionally contain other inert components such as an anti-freezing agent, e.g. propylene glycol, in cases where the mixture is to be stored at or below freezing temperatures; a defoaming agent, e.g. a silicon oil such as RHODASIL supplied by Rhodia Co. and a thickening agent e.g. a carbohydrate polysaccharide such as KELZAN, supplied by Kelco Inc., and other conventional additives employed for color, odor or taste or other optional affect.

The use of lactam polymer in the present mixture permits the use of lower concentration of suspension agent in the concentrate and hence lower concentration of anionic component which in some cases exhibits irritant properties and which causes foaming. Also the presence of lactam polymer allows the use of otherwise incompatible anionic dispersants.

The concentrate of the invention is efficiently prepared by simply homogenizing and wet-milling the components or by extrusion. The above concentrate is then diluted with the desired amount of water by mixing in a high speed mixer for a period of from about 30 minutes to 1 hour.

The concentrates of the present invention can incorporate up to 90% of the active material in its mixture while retaining its stability for at least 1 year or more. On dilution the active component can have a concentration of 10 ppm to 5% in the diluted mixture while retaining stability of 4 hours or more. The combination of the anionic dispersant with the lactam polymer has a synergistic suspension affect in that the dispersing ability of the sum of either component alone is markedly exceeded.

Having generally described the invention, reference is had to the following examples which illustrate preferred embodiments and comparisons of the present concentrate or formulation with those of the prior art.

EXAMPLES 1–31

Preparation of the Suspension Concentrates

The suspension concentrates in Examples 1 through 31 of the following table, with the exception of KELZAN concentrate, were prepared by wet-milling using an Eiger Machinery Model # 100. Before wet milling, the components of the suspension were mixed in a homogenizer equipped with a cooling jacket. Between 70 and 80% loading of the homogenizer with 0.1 cm zirconium beads was employed.

The concentrate mixtures were milled for 10 minutes at 3,000 rpm and the temperature was maintained at −5 to 0° C. The operating conditions of the wet mill included 19 passes of concentrate per minute.

In the case of KELZAN, a 1% aqueous solution was employed and 15.1 g. of this solution was added to 84.0 g. of the wet milled concentrate described above.

The present concentrate mixtures containing anionic dispersant and vinyl lactam polymer produced stable, fine suspensions containing about 90% of particles less than 0.5 microns and a mean volume diameter less than 3.0 microns.

Alternatively, to the above preparation, the particles of the suspension concentrate can be converted into water dispensable granules by means of extrusion where the water dispersed granules, when diluted in water, provide a fine suspension of particles of 5 microns or less.

Method Of Analysis

Suspensibility tests on the present concentrates were performed in 1,000 ppm of water containing 17.5 g CaCl2+ 8.14 g MgCl2 /6H$_2$O in 20 liters of water and 5,000 ppm of hard water according to CIPAC Test # MT 161. The test was run using a calculated weight of the suspension concentrate to provide a 1 wt. % active concentration when diluted into 250 ml of hard water. After 4 hours, 90% of the dispersion was decanted and discarded while the remaining 10% was centrifuged at 2,000 rpm for 15 minutes and then dried and the solid active material was weighed. The results are reported as weight percent suspended active ingredient.

TABLE

Compositions of 41% Chlorothalonil* suspension concentrates and Suspendability data at 1/40 dilution MOREWET D 425 and AGRIMER K 30 SYNERGY

| Ingredients Composition | Wt % | | | | | |
|---|---|---|---|---|---|---|
| | Example 1 | Example 2 | Example 3 | Example 4 | Example 5 | Example 6 |
| Chlorothalonil | 41 | 41 | 41 | 41 | 41 | 41 |
| Kelzan | 0.15 | 0.15 | 0.15 | 0.15 | 0.15 | 0.15 |
| Propylene glycol | 3.5 | 3.5 | 3.5 | 3.5 | 3.5 | 3.5 |

TABLE-continued

| | | | | | | |
|---|---|---|---|---|---|---|
| Proxel GXL | 0.25 | 0.25 | 0.25 | 0.25 | 0.25 | 0.25 |
| Rhodorsil 426 R | 0.2 | 0.2 | 0.2 | 0.2 | 0.2 | 0.2 |
| Primary dispersants | | | | | | |
| Reax 100 M | 0 | 0 | 0 | 0 | 0 | 0 |
| Reax 85A | 0 | 0 | 0 | 0 | 0 | 0 |
| Reax 88B | 0 | 0 | 0 | 0 | 0 | 0 |
| Morewet 425 | 0 | 1 | 0.5 | 2 | 0.33 | 0.17 |
| diSPerse (as 100% solid) | 0 | 0 | 0 | 0 | 0 | 0 |
| Secondary dispersants | | | | | | |
| Agrimer K 30 | 3 | 0 | 2.5 | 0 | 1.67 | 0.83 |
| Agrimer VA 6 | 0 | 0 | 0 | 0 | 0 | 0 |
| Agrimer AL 10 | 0 | 0 | 0 | 0 | 0 | 0 |
| Water | qs to 100% | qs to 100% | qs to 100% | qs to 100% | qs to 100% | qs to 100% |
| 4 h, Suspendability at 1/40, dilution, % suspended | NA (Not applicable, excessive flocculation in the concentrate) | 21 | 91 | 5 | 90 | 96 |

REAX and AGRIMER K 30 SYNERGY
Compositions of 41% Chlorothalonil suspension concentrates and Suspendability data at 1/40 dilution

| Ingredients | Wt % | | | |
|---|---|---|---|---|
| Composition | Example 7 | Example 8 | Example 9 | Example 10 |
| Chlorothalonil | 41 | 41 | 41 | 41 |
| Kel zan | 0.15 | 0.15 | 0.15 | 0.15 |
| Propylene glycol | 3.5 | 3.5 | 3.5 | 3.5 |
| Proxel GXL | 0.25 | 0.25 | 0.25 | 0.25 |
| Rhodorsil 426 R | 0.2 | 0.2 | 0.2 | 0.2 |
| Primary dispersants | | | | |
| Reax 100 M | 0 | 0 | 0 | 0 |
| Reax 85A | 1 | 0.21 | 0 | 0 |
| Reax 88B | 0 | 0 | 1 | 0.21 |
| Morewet 425 | 0 | 0 | 0 | 0 |
| diSPerse (as 100% solid) | 0 | 0 | 0 | 0 |
| Secondary dispersants | | | | |
| Agrimer K 30 | 0 | 0.84 | 0 | 0.84 |
| Agrimer VA 6 | 0 | 0 | 0 | 0 |
| Agrimer AL 10 | 0 | 0 | 0 | 0 |
| Water | qs to 100% | qs to 100% | qs to 100% | qs to 100% |
| 4 h, Suspendability at 1/40, dilution, % suspended | 37 | 92 | 39 | 90 |

| Ingredients | Wt % | | | |
|---|---|---|---|---|
| Composition | Example 11 | Example 12 | Example 13 | Example 14 |
| Chlorothalonil | 41 | 41 | 41 | 41 |
| Kel zan | 0.15 | 0.15 | 0.15 | 0.15 |
| Propylene glycol | 3.5 | 3.5 | 3.5 | 3.5 |
| Proxel GXL | 0.25 | 0.25 | 0.25 | 0.25 |
| Rhodorsil 426 R | 0.2 | 0.2 | 0.2 | 0.2 |
| Primary dispersants | | | | |
| Reax 100 M | 1 | 0.8 | 0.21 | 0.5 |
| Reax 85 A | 0 | 0 | 0 | 0 |
| Reax 88 B | 0 | 0 | 0 | 0 |
| Morewet 425 | 0 | 0 | 0 | 0 |
| diSPerse (as 100% solid) | 0 | 0 | 0 | 0 |
| Secondary dispersants | | | | |
| Agrimer K 30 | 0 | 0 | 0.84 | 2.5 |
| Agrimer VA 6 | 0 | 0 | 0 | 0 |
| Agrimer AL 10 | 0 | 0 | 0 | 0 |
| Water | qs to 100% | qs to 100% | qs to 100% | qs to 100% |
| 4 h, Suspendability at 1/40, dilution, % suspended | 87 | NA (Not applicable, excessive flocculation in the concentrate) | 92 | 94 |

TABLE-continued

REAX/diSPerse and AGRIMER VA 6 SYNERGY
Compositions of 41% Chlorothalonil suspension concentrates and Suspendability data at 1/40 dilution

| Ingredients Composition | Wt % | | | | | |
|---|---|---|---|---|---|---|
| | Example 15 | Example 16 | Example 17 | Example 18 | Example 19 | Example 20 |
| Chlorothalonil | 41 | 41 | 41 | 41 | 41 | 41 |
| Kel zan | 0.15 | 0.15 | 0.15 | 0.15 | 0.15 | 0.15 |
| Propylene glycol | 3.5 | 3.5 | 3.5 | 3.5 | 3.5 | 3.5 |
| Proxel GXL | 0.25 | 0.25 | 0.25 | 0.25 | 0.25 | 0.25 |
| Rhodorsil 426 R | 0.2 | 0.2 | 0.2 | 0.2 | 0.2 | 0.2 |
| Primary dispersants | | | | | | |
| Reax 100 M | 0 | 0.8 | 0 | 0 | 0.1–0.5 | 0.4 |
| Reax 85A | 0 | 0 | 0 | 0 | 0 | 0 |
| Reax 88B | 0 | 0 | 0 | 0 | 0 | 0 |
| Morewet 425 | 0 | 0 | 0 | 0 | 0 | 0 |
| dISPerse (as 100% solid) | 0 | 0 | 0.5 | 0.5 | 0.1–0.5 | 0.1 |
| Secondary dispersants | | | | | | |
| Agrimer K 30 | 0 | 0 | 0 | 0 | 0 | 0 |
| Agrimer VA 6 | 3 | 0 | 0 | 2.5 | 0 | 1.5 |
| Agrimer AL 10 | 0 | 0 | 0 | 0 | 0 | 0 |
| Water | qs to 100% | qs to 100% | qs to 100% | qs to 100% | qs to 100% | qs to 100% |
| 4 h, Suspendability at 1/40, dilution, % suspended | NA (Not applicable, excessive flocculation in the concentrate) | NA (Not applicable, excessive flocculation in the concentrate) | 5 | 90 | 3 Excessive flocculation in the concentrate | 82 |

REAX/diSPerse and AGRIMER K 30 SYNERGY
Compositions of 41% Chlorothalonil suspension concentrates and Suspendability data at 1/40 dilution

| Ingredients Composition | Wt % | | | | |
|---|---|---|---|---|---|
| | Example 21 | Example 22 | Example 23 | Example 24 | Example 25 |
| Chlorothalonil | 41 | 41 | 41 | 41 | 41 |
| Kel zan | 0.15 | 0.15 | 0.15 | 0.15 | 0.15 |
| Propylene glycol | 3.5 | 3.5 | 3.5 | 3.5 | 3.5 |
| Proxel GXL | 0.25 | 0.25 | 0.25 | 0.25 | 0.25 |
| Rhodorsil 426 R | 0.2 | 0.2 | 0.2 | 0.2 | 0.2 |
| Primary dispersants | | | | | |
| Reax 100 M | 0.8 | 0 | 0 | 0.1–0.5 | 0.4 |
| Reax 85A | 0 | 0 | 0 | 0 | 0 |
| Reax 88B | 0 | 0 | 0 | 0 | 0 |
| Morewet 425 | 0 | 0 | 0 | 0 | 0 |
| dISPerse (as 100% solid) | 0 | 0.5 | 0.5 | 0.1–0.5 | 0.1 |
| Secondary dispersants | | | | | |
| Agrimer K 30 | 0 | 0 | 2.5 | 0 | 1.5 |
| Agrimer VA 6 | 0 | 0 | 0 | 0 | 0 |
| Agrimer AL 10 | 0 | 0 | 0 | 0 | 0 |
| Water | qs to 100% | qs to 100% | qs to 100% | qs to 100% | qs to 100% |
| 4 h, Suspendability at 1/40, dilution, % suspended | NA (Not applicable, excessive flocculation in the concentrate) | 5 | 89 | 3 or excessive flocculation in the concentrate | 84 |

*Fungicide: tetrachloroisophthalonitrile.

TABLE

REAX/diSPerse and AGRIMER AL 10 SYNERGY
Compositions of 41% Chlorothalonil suspension concentrates and Suspendability data at 1/40 dilution

| Ingredients Composition | Wt % | | | | | |
|---|---|---|---|---|---|---|
| | Example 26 | Example 27 | Example 28 | Example 29 | Example 30 | Example 31 |
| Chlorothalonil | 41 | 41 | 41 | 41 | 41 | 41 |
| Kel zan | 0.15 | 0.15 | 0.15 | 0.15 | 0.15 | 0.15 |
| Propylene glycol | 3.5 | 3.5 | 3.5 | 3.5 | 3.5 | 3.5 |

TABLE-continued

REAX/dISPerse and AGRIMER AL 10 SYNERGY
Compositions of 41% Chlorothalonil suspension concentrates and Suspendability data at 1/40 dilution

| Ingredients Composition | Wt % | | | | | |
|---|---|---|---|---|---|---|
| | Example 26 | Example 27 | Example 28 | Example 29 | Example 30 | Example 31 |
| Proxel GXL | 0.25 | 0.25 | 0.25 | 0.25 | 0.25 | 0.25 |
| Rhodorsil 426 R | 0.2 | 0.2 | 0.2 | 0.2 | 0.2 | 0.2 |
| Primary dispersants | | | | | | |
| Reax 100 M | 0 | 0.8 | 0 | 0 | 0.1–0.5 | 0.4 |
| Reax 85 A | 0 | 0 | 0 | 0 | 0 | 0 |
| Reax 88 B | 0 | 0 | 0 | 0 | 0 | 0 |
| Morewet 425 | 0 | 0 | 0 | 0 | 0 | 0 |
| dISPerse (as 100% solid) | 0 | 0 | 0.5 | 0.5 | 0.1–0.5 | 0.1 |
| Secondary dispersants | | | | | | |
| Agrimer K 30 | 0 | 0 | 0 | 0 | 0 | 0 |
| Agrimer VA 6 | 0 | 0 | 0 | 0 | 0 | 0 |
| Agrimer AL 10 | 3 | 0 | 0 | 2.5 | 0 | 1.5 |
| Water | qs to 100% | qs to 100% | qs to 100% | qs to 100% | qs to 100% | qs to 100% |
| 4 h, Suspendability at 1/40, dilution, % suspended | NA (not applicable, excessive flocculation in the concentrate) | NA (Not applicable, excessive flocculation in the concentrate) | 5 | 92 | 3 Excessive flocculation inthe concentrate | 82 |

In the above examples, activated carbon, zinc oxide, titanium dioxide or iron oxide can be substituted for the hydrophobic agriculturally active chemical to provide stable particle suspensions of 5 or less micron size. Similarly, phthalocigamine dye or an azo dye, e.g. triphenyl methane derivatives.

What is claimed is:

1. An aqueous suspension concentrate containing, by weight of the total aqueous concentrate, of (a) between about 20 and about 90 wt. % of an active hydrophobic material; (b) between about 0.1 and about 15 wt. % of a polymeric anionic dispersing agent which consists of a mixture of the sodium salt of an alkyl vinyl ether/maleic acid half ester copolymer or an alpha-olefin/maleic acid copolymer and a lignosulfonate, a lignosulfonate metal salt or a sulfonated naphthalene/formaldehyde condensate, and (c) between about 0.1 and about 10 wt. % of a N-vinyl lactam polymer selected from the group consisting of homo- and co-polymers of N-vinyl pyrrolidone and N-vinyl caprolactam and mixtures thereof.

2. The aqueous suspension concentrate of claim 1 wherein said vinyl lactam polymer has a weight average molecular weight of from about 5,000 to about 100,000.

3. The aqueous suspension concentrate of claim 2 wherein said vinyl lactam polymer is a copolymer of N-vinyl pyrrolidone, dimethylaminoethylmethacrylate and N-vinyl caprolactam.

4. The aqueous suspension concentrate of claim 1 wherein said anionic dispersing agent contains a sulfonated naphthalene formaldehyde condensate.

5. The aqueous suspension concentrate of claim 1 wherein said anionic dispersing agent is selected from the group consisting of a lignosulfonate and a metal salt thereof.

6. The aqueous suspension concentrate of claim 1 containing between about 0.5 and about 10 wt. % anionic dispersing agent and between about 0.3 and about 5 wt. % lactam polymer.

7. The aqueous suspension concentrate of claim 1 wherein the mole ratio of anionic dispersant to lactam polymer is between about 0.1:1 and about 3:1.

8. The aqueous suspension concentrate of claim 1 optionally contains up to 10 wt. % of a excipient selected from the group of an anti-freezing agent, a defoaming agent, a thickening agent and mixtures thereof.

9. The aqueous suspension concentrate of claim 1 wherein said active hydrophobic material is a hydrophobic agricultural chemical or a mixture of said chemicals.

10. A formulation containing between about 0.1 and about 5 wt. % of the concentrate of claim 1 or 9 and water.

11. The aqueous suspension of claim 1 wherein said active hydrophobic material is selected from the group consisting of a nematocide, fungicide, insecticide, herbicide, mulliscide, fertilizer, plant nutrient, plant growth accelerant or regulator and mixtures thereof.

12. The aqueous suspension of claim 11 wherein said active hydrophobic material is chlorothalonil.

13. The aqueous suspension of claim 2 wherein the dispersing agent contains a sulfonated naphthalene/formaldehyde condensate, the N-vinyl lactam polymer is poly(N-vinyl pyrrolidone) and the active material is chlorothalonil.

* * * * *